United States Patent

Cox

[11] Patent Number: 5,105,476
[45] Date of Patent: Apr. 21, 1992

[54] SPORTS VISOR WITH SWEATBAND AND REMOVAL VISOR

[76] Inventor: Cheryl J. Cox, 4054 Stone Canyon, Sherman Oaks, Calif. 91403-4541

[21] Appl. No.: 695,628

[22] Filed: May 3, 1991

Related U.S. Application Data

[63] Continuation-in-part of Ser. No. 112,133, Oct. 21, 1987.

[51] Int. Cl.⁵ .............................................. A61F 9/00
[52] U.S. Cl. .............................................. 2/12; 2/181; 2/DIG. 11
[58] Field of Search ................ 2/10, 12, 15, 181, 196, 2/199, 209.1, 422, 425, DIG. 11

[56] References Cited

U.S. PATENT DOCUMENTS

| | | |
|---|---|---|
| 121,538 | 5/1840 | Dressler . |
| 226,598 | 4/1873 | Yeeda ................... D2/247 |
| 263,092 | 2/1882 | Fay ....................... D2/241 |
| 267,752 | 2/1883 | Fairbrother .......... D2/241 |
| 272,865 | 3/1884 | Edelmann ............ D2/241 |
| 276,854 | 12/1884 | Stockton ............... D2/241 |
| 285,021 | 8/1886 | Chandler .............. D2/241 |
| 288,741 | 3/1887 | Holt ...................... D2/514 |
| 535,143 | 3/1895 | Mendelson . |
| 757,853 | 4/1904 | Wickersham . |
| 1,232,992 | 7/1917 | Stering . |
| 1,484,042 | 2/1924 | Smile .................... 2/12 |
| 1,506,664 | 8/1924 | Pickard . |
| 1,575,219 | 3/1926 | McClay et al. . |
| 1,638,756 | 8/1927 | Wallman . |
| 1,809,956 | 6/1931 | Wrenshall . |
| 2,016,210 | 10/1935 | Mann ..................... 2/171 |
| 2,019,028 | 10/1935 | Sternberg .............. 2/12 |
| 2,092,805 | 9/1937 | Jones ...................... 2/12 |
| 2,265,530 | 12/1941 | Kleinman .............. 2/181 |
| 2,696,007 | 12/1954 | Larkin et al. ......... 2/171 |
| 2,747,196 | 5/1956 | Kaye ...................... 2/175 |
| 4,023,212 | 5/1977 | Huffman ............... 2/197 |
| 4,096,589 | 6/1978 | Goldstein .............. 2/12 |
| 4,393,519 | 7/1983 | Nicastro ................ 2/12 |
| 4,394,782 | 7/1983 | Wasson ................. 2/181 |
| 4,547,903 | 10/1985 | Brown et al. ......... 2/12 |
| 4,575,875 | 3/1986 | Dawson ................. 2/12 |
| 4,578,822 | 4/1986 | Schmidthaler ........ 2/12 |
| 4,621,378 | 11/1986 | Hatchman ............. 2/12 |
| 4,630,317 | 12/1986 | Brown et al. ......... 2/12 |
| 4,712,254 | 12/1987 | Daigle ................... 2/DIG. 11 |
| 4,811,430 | 3/1989 | Janusz ................... 2/DIG. 11 |
| 4,856,116 | 8/1989 | Sullivan ................. 2/12 |
| 4,873,726 | 10/1989 | Tapia ..................... 2/10 |
| 5,046,195 | 9/1991 | Koritan ................. 2/199 |

FOREIGN PATENT DOCUMENTS

| | | | |
|---|---|---|---|
| 2039725 | 8/1980 | United Kingdom ........ | 2/12 |
| 2070413 | 9/1981 | United Kingdom ........ | 2/209.1 |

Primary Examiner—Werner H. Schroeder
Assistant Examiner—Diana L. Biefeld
Attorney, Agent, or Firm—Lyon & Lyon

[57] ABSTRACT

A sports visor having a sweatband and a normally flat, sheet-like removable visor fixed to the sweatband. The visor is comprised of a top face and a bottom face and may be secured to the sweatband with a securing means located on the bottom face of the visor.

16 Claims, 6 Drawing Sheets

SPORTS VISOR WITH SWEATBAND AND REMOVAL VISOR

This application is a continuation-in-part of pending application Ser. No. 07/112,133 filed Oct. 21, 1987, which disclosure is fully incorporated herein by reference.

BACKGROUND OF THE PRESENT INVENTION

The field of the present invention relates to headgear and, more specifically, to sweatbands with removable visors.

Recreational and professional athletes utilize and require various types of headgear depending upon factors such as the type of sport they are involved in, the weather conditions in which the headgear is to be worn and so forth. In each instance the athlete selects a headgear to provide several functions which may include, for example, a sweatband for absorbing perspiration, a headband which is generally lighter than a sweatband for holding the hair back away from the face, a visor for protecting the eyes and face from the sun, a cap for keeping the head warm or protecting the head from rain or any combination thereof. Other considerations for selecting a headgear may include comfort, the ability of the headgear to remain secure around an athlete's head without slipping, and whether the headgear is made of safe or soft materials that will not injure the athlete in, for example, a fall or collision with another athlete.

Along the same lines, an athlete requires a sports visor that is versatile enough to keep the sun out of the wearer's eyes without obstructing his field of vision. One of the primary problems with existing headgear/visor combination is that the visors are designed to extend from a fixed position underneath the base or bottom edge of the headgear. However, this positions the visor too close to the top of the wearer's eyes thereby obstructing the wearer's vision, both, upwardly and peripherally. Although this headgear/visor combination will shield the wearer's eyes from the sun, it will also block the wearer's field of vision making it difficult to, for example, adequately follow the trajectory of a fast-moving tennis ball. As a result it is rare to see professional athletes in fast moving sports such as tennis, wearing visors. A tennis player, for example, concerned with having a visor that blocks the sun, will forego using such a visor if it also blocks his forward and/or peripheral vision. As an alternative, some headgear such as the type used by baseball and volleyball players permits the visor to fold or flip upwardly away from the wearer's eyes to provide a greater range of vision. But, in this upwardly folded position, the visor does not protect the wearer's eyes from the sun requiring constant repositioning of the visor which may detrimentally spoil the athlete's concentration during the game.

Another important feature often desired is a sweatband with a removable visor that permits the sweatband to be worn alone. For example, a visor may not be required on a cloudy morning but may be required if the sun comes out later in the day. Also, the sweatband may be desired merely to hold the hair back away from the face. Along the same lines, interchangeable visors that can be positioned in different locations on the sweatband are also desired. Although removable visors exist, they can only be secured in singular or limited positions on the headgear. As a result the wearer is unable to adjust the visor to place it in a desired position on the sweatband or headgear.

It is also sometimes desirable to have a sweatband that permits a variety of different visors to be interchanged or used simultaneously. For example, a neck drape or cloth that hangs down the back of the visor may be desired to protect the back of the neck from the sun. Similarly, a visor that surrounds the entire circumference of the sweatband may be desired. However, there are many problems in existing headgear/visor combinations that prevent such an interchangeable feature. For example, many headgear/visor combinations provide only singular affixation means for mounting the visors and/or may not have the room or the means to mount more than one visor. In addition, they often require involved procedures to secure the visors to the headgear such as threading a headband through holes provided in the visor, buttoning the visor to the headgear, removing the headband to attach to the visor and so forth.

Another very important feature that is desired is a durable sweatband that adequately absorbs perspiration and/or supports a visor as compared with the typical headband which is merely a thin strip of non-absorbent material such as leather or an elastic strip of minimally absorbent material such as terry cloth. In other words, most headbands absorb very little moisture. When subjected to substantial amounts of perspiration, they become soggy to the point where they are uncomfortable or useless to wear. In addition, these headbands often lose their ability to support a visor.

Another desired feature in a sports visor is a sturdy and comfortable headgear and visor that can be securely worn and yet will not fly off the wearer's head when encountering substantial or high wind resistance. Oftentimes, for example, a baseball player loses his baseball cap while sprinting towards first base or to catch a fly ball. Although the baseball player is able to eventually retrieve his cap, another athlete, such as a sailor on a racing boat; may not have that luxury. Several problems contribute to the inability of a headgear to support a visor. One aspect is that the visor often exceeds the weight of the headgear, enabling wind or the like to pull the headgear off the head upon encountering wind or the like. Another aspect is that the visors, being secured from underneath the base or bottom edge of the headgear, may contact the wearer's head, making it uncomfortable or impossible for the wearer to tighten the headgear around his head, and leading to slippage or the like. That is, tightening the headgear causes the visor edge to dig into the wearer's forehead.

Along the same lines headgear with removable visors often fall apart or separate when encountering substantial wind resistance or the like. In other words, the visor may be blown off of or separate from the headgear. One reason for this problem is that the associated visors are too heavy and/or thick to be supported by the headgear or, alternatively, the headgear is too light to adequately hold the visor. Still further, a related problem is that the headgear is typically adjusted to conform to the wearer's head with an elastomeric band or the like, which typically loses its elasticity upon washing. Consequently, over time, these bands may lose their ability to be adjusted securely against the head.

Comfort and safety are also important features required in a sports visor This requires, for example, that the headband be made of a soft, sturdy material and that the visor be lightweight, flexible and without hard, sharp edges. Many existing sports visors, for example, utilize metal buttons, plastic headband adjusters, thin ropes or pre-formed and molded visors, which all can be painful when pressed against the wearer's head in order to secure them.

SUMMARY OF THE INVENTION

The present invention is directed to a sports visor having a sweatband and a removable visor. To this end, a sweatband is provided having an outside face and an inside face wherein the outside face includes an affixation means for retaining a visor in various locations thereon. A thin, flat, or sheet-like visor having a top face and a bottom face is also provided wherein said bottom face comprises a securing means for securing the visor in various positions on the front face of the sweatband.

Accordingly, it is an object of the present invention to provide a versatile sports visor having a sturdy, durable and highly absorbent sweatband that is designed to support one or several removable visors such that the visors can be angled or positioned on the sweatband to provide maximum protection from the sun in order to protect the wearer's eyes, face and/or neck while minimally obstructing the wearer's range of vision.

Another object of the present invention is to provide a sweatband having an internal stuffing that absorbs and transports moisture away from the inside face of the sweatband towards the outside face of the sweatband.

Another object of the present invention is to provide a normally flat, sheet-like visor (which is capable of flexing into a curved shape while secured to the visor) and a means for securing the visor to the sweatband without including an additional curved forehead portion on the visor.

Another object of the present invention is to provide a plurality or system of removable and interchangeable sweatbands and visors that can be utilized in connection with each other.

Another object of the present invention is to provide a sports visor that, in addition to protecting the wearers eyes, also protects the entire face and/or neck from the ultraviolet rays of the sun.

Other and further objects and advantages will appear hereinafter.

BRIEF DESCRIPTION OF THE DRAWINGS

FIG. 7 is a top right perspective view of the sweatband illustrated in FIG. 1 without the visor.

DETAILED DESCRIPTION OF THE PREFERRED EMBODIMENT

Figure 1:
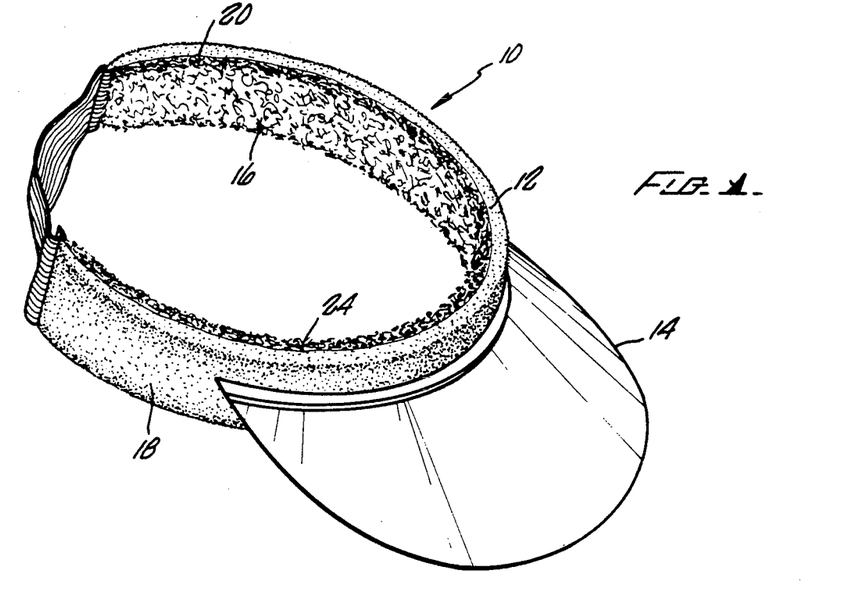
FIG. 1 is a top right perspective view of a first embodiment of the present invention.

Turning in detail to the drawings, FIG. 1 illustrates a sports visor 10 having a sweatband 12 and a visor 14 attached thereto. The sweatband 12 is comprised of an inside face 16, an outside face 18, a top edge 20 and a bottom edge 22. The inside face 16 is an absorbent material such as terry cloth, fleece, COOLMAX ® manufactured by DuPont, MICROFT ® manufactured by Teijin COOLMAX ® manufactured by DuPont, MICROFT ® manufactured by Teijin or any other suitable material designed to absorb and transport moisture such as perspiration. The absorbent material extends from under the bottom edge 22, up to and over the top edge 20 and around the inside face 16 of the sweatband 12. In other embodiments, the material utilized on the inside and/or outside faces may be changed to better suit the activity in which the wearer is involved. For example, it may be desirable to utilize a waterproof material when the sports visor 10 is to be worn in connection with a watersport such as windsurfing. Similarly, a warm or heat retaining fabric may be used when the sports visor 10 is to be worn in connection with a winter sport such as skiing.

Figures 1, 4, 5, 6, 8:
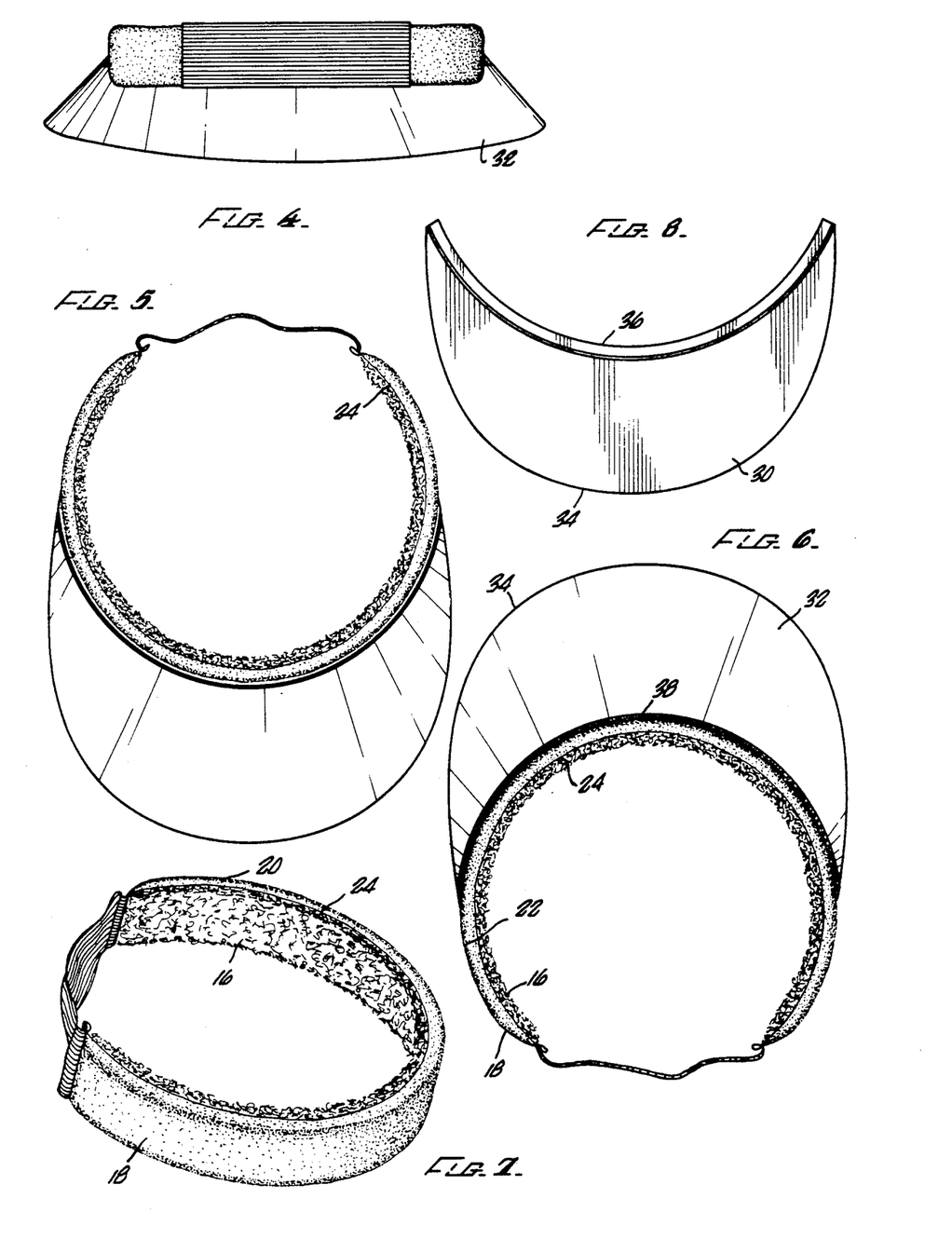
FIGS. 2-6 are, respectively, front, side, rear, top and bottom views of the present invention illustrated in FIG. 1.
FIG. 8 is a top view of the visor of the present invention prior to being connected to the sweatband.
Figure 2:
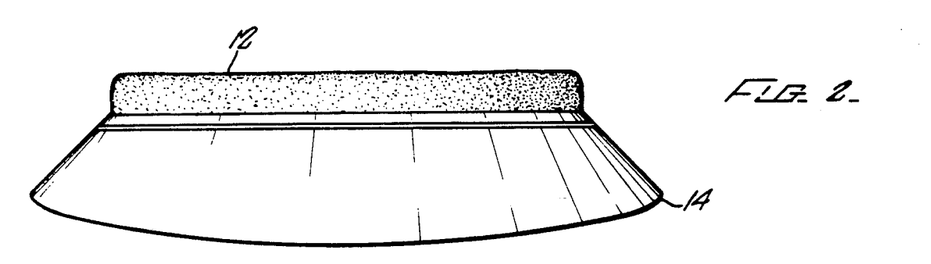
Figures 10, 11, 11A:
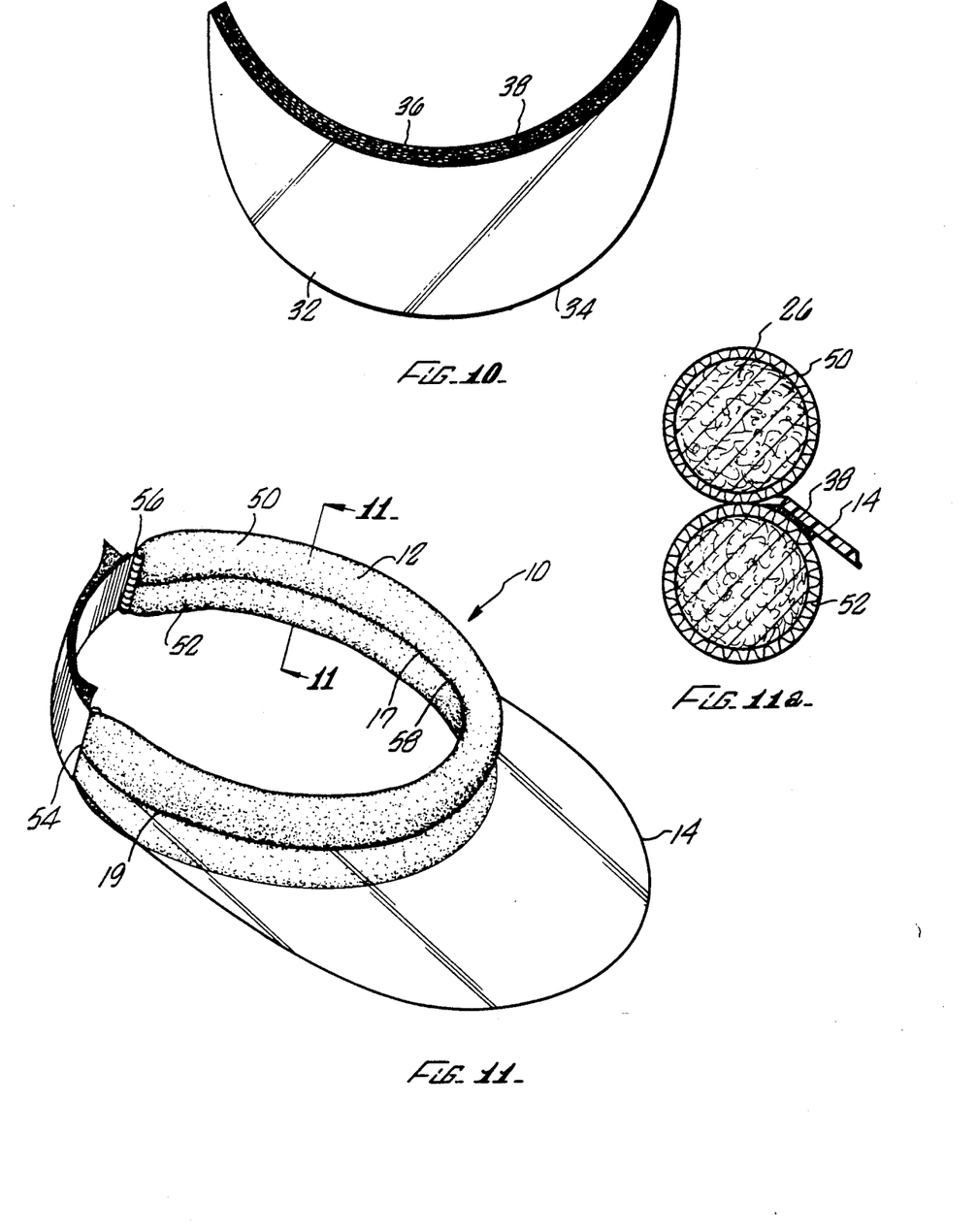
FIG. 10 is a bottom view of the visor of the present invention prior to being connected to the sweatband.
FIG. 11 is a top right perspective view of a second embodiment of the present invention.
FIG. 11a is a cross-section along section 11a—11a in FIG. 11 of the sweatband of the second embodiment.

The outside face 18 is a flat planar surface comprised of a smooth fabric or fabric-like material which has the ability to serve as an affixation means for retaining the visor 14 on the sweatband 12 such as brushed nylon, polyester and other fabrics. The fabric-like material extends from under the bottom edge 22 up to and over the top edge 20 and around the entire outside face 18 of the sweatband 12. Since the fabric is on the outside face 18 it may be desirable to provide a visually appealing fabric in order to decorate or personalize the sweatband 12. The inside face 16 and outside face 18 are sewn, interwoven or otherwise connected along a seam 24 on the top edge 20 as illustrated in FIGS. 1 and 5 and on the bottom edge 22 as illustrated in FIG. 6. Together the fabric-like material on the outside face 18 and the absorbent material on the inside face 16 serve as a covering around a highly absorbent moisture absorbing means or internal stuffing 26. The moisture absorbing means inside the sweatband 12 is comprised of a stuffing 26 which serves to remove or transport moisture such as perspiration away from the inside face 16 of the sweatband 12 towards the outside face 18. The absorbent stuffing 26 may be provided in a portion of or in the entire sweatband and consists of natural or man-made soft fiber-fill such as bound or trussed cotton. The stuffing 26 is secured or sewn to the exterior fabric-like material of the outside face 18 and/or the inside face 16 which helps to prevent the stuffing 26 from becoming loose or clumping or bunching up inside the sweatband 12. Furthermore, all the materials of the sweatband 12 are machine-washable which allows the sweatband 12 to be cleaned and reused. The stuffing 26 also provides a thick cushion or cushion-like sweatband 12 that is soft, comfortable and safe to wear yet heavy and durable enough to support a visor 14 even when wet. One embodiment of the present invention utilizes approximately two (2) ounces of internal stuffing 12 inside an average size sweatband 12. Similarly, a greater or lesser amount of internal stuffing may be utilized. A second embodiment of the present invention as shown in FIG. 11a illustrates the stuffing 26 as used in the other various embodiments.

The flat, planar surface of the inside face 16 of the sweatband 12 is adapted for contacting a wearer's forehead and designed to provide sufficient contact to support the sweatband 12 around the wearer's head. In one embodiment, for example, the width of the sweatband 12 from the top edge 20 to the bottom edge 22 ranges from approximately one inch to approximately three inches while the thickness from the inside face 16 to the outside face 18 is approximately one quarter inch. The length of the sweatband 12 will vary to fit various head sizes and purposes. In one embodiment, for example, the sweatband is approximately seventeen and one half (17-½) inches long interconnected with an elastic fastening means 40 which is approximately six and one half (6-½) inches in length. Of course, other dimensions are possible and can be provided to suit particular needs. For example, the sweatband and/or elastic fastening means may be shorter to fit a smaller head and longer to fit a larger head although the elastic fastening means which can range from, for example, approximately one (1) inch in length to approximately twelve (12) inches in length, can also be stretched to accommodate variations in head sizes. Also, more rigorous sports may require thicker and more absorbent sweatbands 12 to compensate for greater amounts of perspiration. Similarly, a sweatband 12 used merely to hold back the wearer's hair may be lighter and thinner.

The combination of a heavy, durable sweatband 12 permits the sweatband 12 to support a lightweight visor 14 affixed thereto. In one embodiment of the present invention the visor 14 weighs less than one (1) ounce and can be at least as light as 0.50 ounces. Thus, a particular embodiment having a sweatband 12 weighing two ounces and a visor weighing one-half an ounce will have a sweatband-to-visor weight ratio of approximately 4:1. Of course, this ratio will vary depending upon factors such as the size of the sweatband 12, the amount of stuffing included in the sweatband and the weight of the visor 14. In contrast, existing headband/visor combinations have a weight ratio wherein the weight of the visor exceeds the weight of the headband making it difficult for the headband to support the visor.

Furthermore, the visor 14 of the present invention is secured to the outside face 18 of the sweatband 12 as distinguished from underneath the base or bottom edge 22 of the sweatband 12 as in other versions of headgear that support visors. As a result, the rim or rear edge 36 of the visor 14 does not press or "dig" into the wearer's forehead when the sweatband 12 is tightened around the wearer's head. Thus, the sweatband 12 can be secured relatively tightly around the wearer's head without discomfort to the wearer to insure that the sweatband 12 and visor 14 remain on the wearer's head even when subjected to substantial wind resistance and the like.

The fabric or fabric-like material on the outside face 18 serves as an affixation means for retaining the visor 14 in various locations on the outside face 18 and, if desired, on the top edge 20 and bottom edge 22 of the sweatband 12. The fabric or affixation means extends around the entire outside circumference or outside surface of the sweatband 12 and, although visible even when the visor 14 is attached to the sweatband 12, is not recognized as an affixation means. The integrity of the sweatband design is such that the entire outside circumference or outside surface is one fabric that functions as the affixation means. Thus, utilizing a colorful or artistic fabric-like material for the affixation means provides a visually appealing sweatband 12. Along the same lines, the affixation means can be limited to only a portion of the outside surface.

Figure 14:
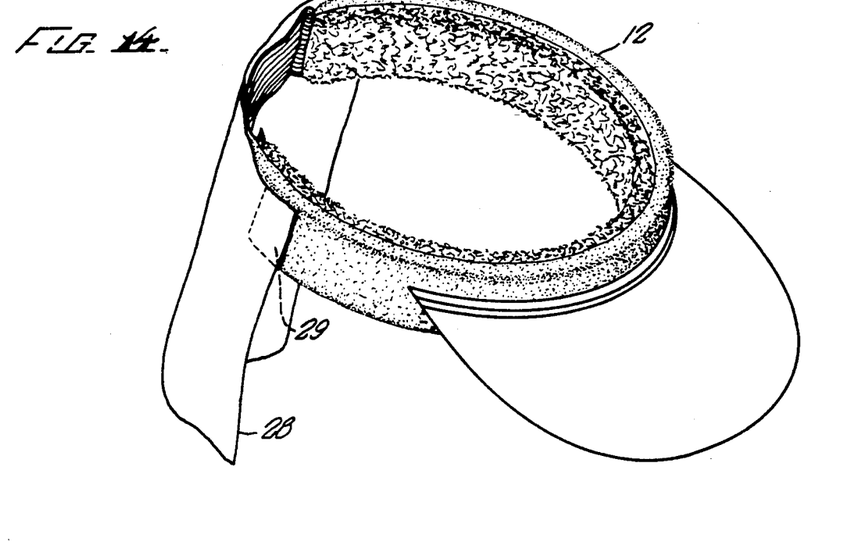
FIG. 14 is a third embodiment of the present invention illustrating a neck drape visor made of cloth that hangs down the back of the wearer's head over the wearer's neck secured to a sweatband along with a visor of the first embodiment.
Figure 15:
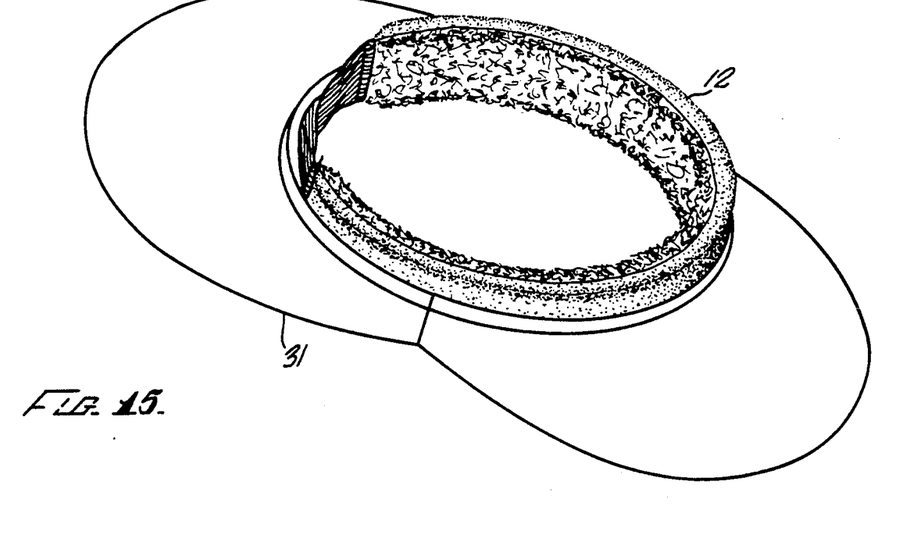
FIG. 15 is a fourth embodiment of the present invention illustrating a visor that extends around the entire outside circumference of a sweatband.
Figure 16:
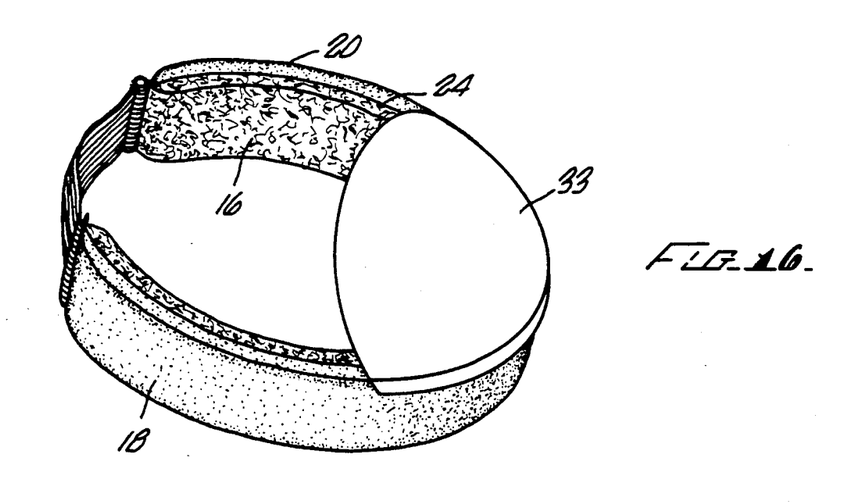
FIG. 16 is a fifth embodiment of the present invention illustrating a flip-top visor.

The combination of using a fabric and visible affixation means around the entire circumference of the sweatband 12 serves a dual purpose. It provides a versatile sweatband 12 that has sufficient room or space to permit one or more interchangeable visors 14, such a visors having different purposes, to be simultaneously mounted thereon. It is also visually appealing and allows an athlete to exhibit such things as team colors. In this regard, a plurality or kit of interchangeable sweatbands 12 having a variety of different purposes, colors or designs may be provided or used with an individual visor 14. Likewise, a plurality or kit of inter-changeable visors 14 having a variety of different purposes, colors or designs may be provided or used with an individual sweatband 12. For example, as illustrated in FIG. 14, a neck drape visor or neck guard 28 made of cloth or other suitable materials and which hangs off the back of the sweatband 12 for protecting the back of the wearer's neck can be provided. As illustrated in FIG. 15, a visor 31 that extends around the entire circumference of the sweatband 12 to protect both the back of the wearer's neck and the wearer's eyes can also be provided. As illustrated in FIG. 16 a flip-top visor 33 for protecting the top of the wearer's head and/or forehead can also be provided. The flip-top visor 33 can be a visor 14 of the first embodiment turned upside down or it can be a smaller version of the visor 14. Similarly, the flip-top 33 can be slightly curved with a concave portion facing the wearer's head and a convex portion facing away from the wearer's head.

Figure 9:
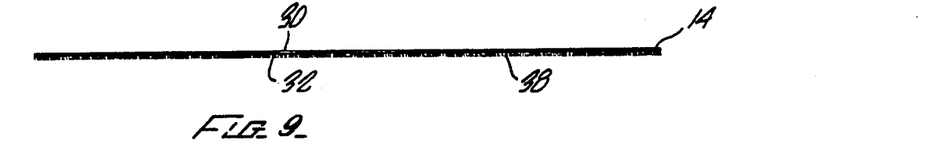
FIG. 9 is a rear view of the visor of the present invention prior to being connected to the sweatband.

As illustrated in FIGS. 8, 9 and 10, a first embodiment of the removable or detachable visor 14 is comprised of a top face 30, a bottom face 32, a convex shaped front edge 34, a concave shaped rear edge 36 and a securing means 38 for securing the visor in various positions on the outside face 18 of the sweatband. The visor 14 is crescent-shaped when viewed from the top or bottom and is very thin, flat and sheet-like when viewed from the side. As illustrated in FIG. 9, the visor is normally flat when not secured to the headboard although normally curved visors can be adapted to be utilized in the present invention. In one embodiment of the present invention the visor 14 is approximately 0.023 millimeters thick but can also range between 0.010 millimeters to 0.025 millimeters. Of course, other thicknesses are envisioned without departing from the inventive concepts herein. The visor 14 may be comprised of any flexible and lightweight material that permits the visor 14 to be easily stored or carried in, for example, a side pocket of a tennis racket face cover. Similarly, the material may be made of a translucent, opaque or imprintable-type plastic or a material that provides ultraviolet protection. In other embodiments, the visor 14 material may be made of cloth, such as the neck drape visor 28 in FIG. 14, or any other material that permits the visor 14 to be flexed or supported by the sweatband 12 as described herein.

The visor 14 is shaped and designed so as not to obstruct the wearer's forward or peripheral vision when secured to the sweatband 12. For example, earlier headgear/visor combinations secure the visor underneath the base of the headgear. However, positioning the visor so low on the headgear places the visor directly over the wearers eyes when the wearer puts the headgear on thereby impairing the wearer's range of vision in the upward and sideways directions. This requires the wearer to arch his head further backwards to see upwardly and to turn his head further to each side to see in these side directions.

In the alternative, other headgear/visor combinations secure the visor to the front of the headgear utilizing some variation of a forehead portion securing means shaped or curved to the configuration of the forehead In other words, the visor is either preformed with or secured to a forehead portion which is a wide planar surface designed to rest on or cover the forehead such that the visor extends perpendicularly from the base of the forehead portion. The curved forehead portion (i.e. —not the visor itself) is secured to the headgear. This forehead portion may range anywhere from a width of one to three or more inches which rests upon the wearer's forehead. The present invention uses neither of these previously mentioned alternatives. It does not employ a planar surface or forehead portion substantially perpendicular to the visor which serves as the securing means.

The present invention provides a securing means 38 underneath or on the bottom face 32 of the visor 14. Thus, the visor 14 or bill itself is secured to the sweatband 12. As best illustrated in FIG. 10, the securing means 38 is comprised of a thin Velcro TM strip sewn or otherwise affixed into or along the rear edge 36 on the bottom face 32 of the visor. Thus, the securing means 38 is parallel to the visor 14. Even with the securing means 38, the visor 14 is substantially flat and sheet-like when viewed from the side as illustrated in FIG. 9. The positioning of the securing means 38 on the rear edge 36 on the underside or bottom face 32 of the visor 14 eliminates the need for including a forehead portion on the visor 14 in order to mount or mate the visor 14 to the sweatband 12.

The securing means 38 employed also permits the visor 14 to be centered on the front of outside face 18 of the sweatband 12 or mounted anywhere on the outside face or circumference of the sweatband 12. As illustrated in FIG. 10, the securing means 38 is a single strip of Velcro TM material interconnected along the entire concave rear edge 34 on the bottom face 32. The securing means 38 can be adhesively applied or sewn to the visor 14. In addition, the securing means 38 can be provided with a finished edge for decorative purposes using self-colored Tricot binding or decorative binding. In one embodiment, the Velcro TM strip 38 is approximately 5/16 of an inch wide with a finished edge. However, alternative embodiments may include thinner or wider strips and/or a plurality of shorter strips of securing means 38 spaced along the inside or rear edge 34. For example, as illustrated in FIG. 14, the neck drape visor 28 is comprised of two short strips 29 of securing means.

Figure 3:
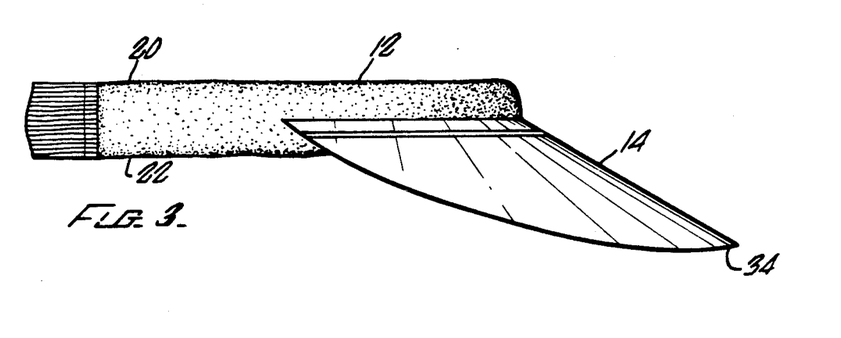

In order to secure or fasten the visor 14 to the sweatband 12, the securing means 38 of the visor 14 is merely pressed onto the outside face 18 of the sweatband 12. Since the entire outside face 18 is the affixation means it is not necessary to remove the sweatband 12 in order to affix the visor 14 as in other more complex headgear/visor combinations. The wearer merely positions the visor 14 in the desired position and presses it onto the sweatband 12. As illustrated in FIG. 3, placing the bottom rear edge 36 of the visor 14 against the outside face 18 causes the flexible visor to bend, forming a curved visor 14 which flexes or angles to provide a downwardly curving visor 14 to shade the wearer's eyes. Alternatively, the visor 14 can be secured to the sweatband 12 without bending or flexing the visor such that the visor 14 extends substantially perpendicular to the sweatband 12 without curling.

Although the visor 14 is illustrated in FIG. 1 as being vertically centered on the sweatband 12, the visor 14 can be positioned in the most desirable location on the sweatband 12 to obtain the greatest range of visibility or to obtain the maximum amount of protection from the sun. The Velcro TM strip 38 may be secured higher up, near to, or directly on the top edge 20 or lower near the bottom edge 22. If the visor 14 is turned upside down, it can be secured directly on the bottom edge 22 to extend outwardly from the base of the sweatband 12. Similarly, the visor 14 can be placed horizontally or diagonally across the sweatband 12 so as to angle over the wearer's eyes or positioned around the circumference of the sweatband 12. For example, the visor 14 can be secured to the rear outside face 18 of sweatband 12 to shade the wearer's neck. Similarly, a plurality of visors 14 designed to serve different purposes can be attached at one time. For example, a visor 14 can be secured t front of the sweatband 12 a flip-top 31 can be secured above the visor 14 and a neck drape visor 28 can be secured to the rear of the sweatband 12. As another example, the visors 14 can be layered such that one visor 14 is secured above a second visor 14.

The sweatband 12 is further comprised of an adjustable fastening means 40 to allow the sweatband 12 to be adjusted to fit various size heads. As illustrated in FIG. 1, the fastening means 40 is an elastic strip sewn to both ends of the sweatband from the top edge 20 to the bottom edge 22. Alternatively, and in a second embodiment as illustrated in FIG. 11, the fastening means 40 may consist of a hook and loop type closure each portion of which is approximately three (3) inches long in one embodiment but which can range in length, for example, from one (1) inch to several inches. Other embodiments of the fastening means 40 include a series of elastic strips, two loose ends of cloth which can be tied together, as well as any other fastening means that permits the sweatband to be adjusted to fit various size heads.

Figure 12:
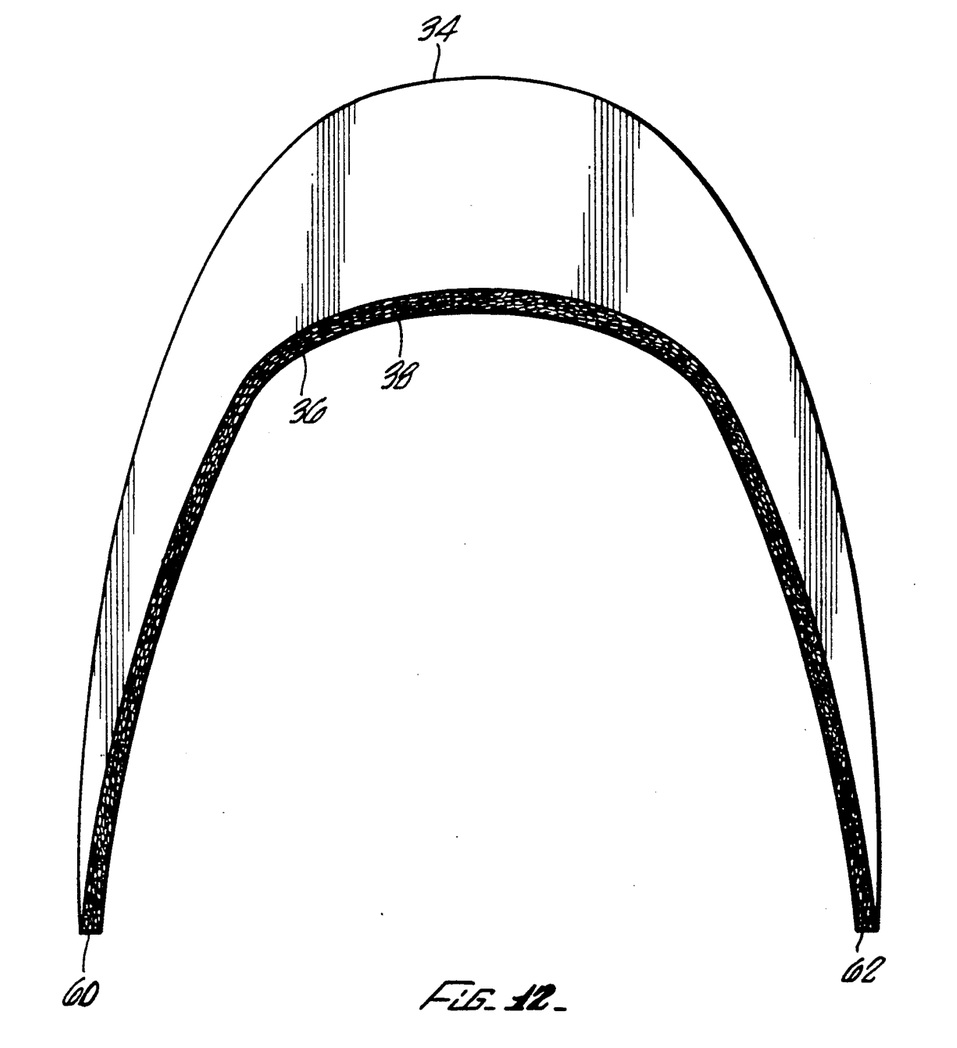
FIG. 12 is a bottom view of a visor utilized in the second embodiment of the present invention prior to being connected to the sweatband.
Figure 13:
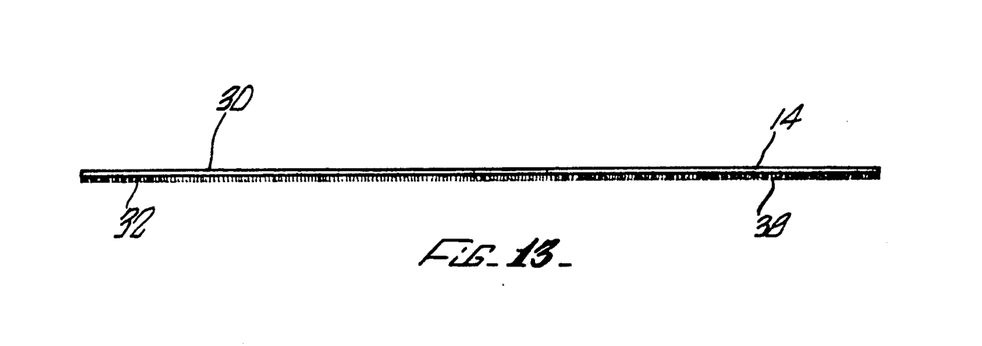
FIG. 13 is a rear view of the visor utilized in the second embodiment of the present invention prior to being connected to the sweatband.

As illustrated in FIGS. 11-13, a second embodiment of the present invention is shown. The elements of the second embodiment are numbered to correspond to similar elements in the first embodiment. Since many of the elements have already been addressed with respect to the first embodiment, the second embodiment will primarily address the differences that exist in the second embodiment.

The second embodiment of the sports visor 10 is comprised of a sweatband 12 having a first tubular element 50 sewn or otherwise interconnected to a second tubular element 52, a fastening means 40 for fastening a first end 54 of the sweatband 12 to a second end 56 of the sweatband 12, and a visor 14 having a securing means 38 for securing the visor 14 to the sweatband 12. Each of the tubular elements 50, 52 are merely smaller versions of the first embodiment of the sweatband 12. In addition, several tubular elements can be utilized to form the sweatband 12.

The sweatband 12 is comprised of an inside face 16 and an outside face 18 but differs from the first embodiment, for example, because it is provided with an inside ridge 17 and an outside ridge 19 formed along a seam 58 between the first and second tubular elements 50, 52 where they are interconnected or sewn together. The material utilized on the inside face 16 and outside face 18 of the second embodiment may be the same materials utilized on the inside face 16 and outside face 18 the first embodiment, respectively. In the alternative, the entire surface of the first and second tubular elements 50, 52 may be comprised of the a smooth fabric or fabric-like material such as brushed nylon or other fabric which has the ability to serve as an affixation means for retaining the visor 14 on the sweatband.

As illustrated in FIGS. 11–13, the visor 14 is substantially similar to the visor 14 described in the first embodiment. However, the visor 14 is provided with two ends 60, 62 that extend around the circumference of the sweatband 12 until it touches the edges of the fastening means 40. A securing means 38 is sewn into or otherwise connected to the bottom face 32 of the visor 14 along the inside or rear arcuate edge 36. Although the visor 14 is secured to the outside ridge 19 of the sweatband 12 which provides a natural ledge for resting the visor 14, it can also be secured anywhere between the top and bottom edges 20, 22. Similarly, the outside ridge 19 may be provided with a second securing means for mating with the first securing means 38 on the visor.

A fastening means 40 is also provided for securing the two distal ends 54, 56 of the sweatband together. The fastening means 40 utilized in the second embodiment differs from the first embodiment in that it is comprised of a hook and loop type connection.

Thus, a sports visor is disclosed which provides a truly functional and absorbent sweatband with one or more thin, flat removable visors and other protective shields that can be positioned relative to the sweatband to allow the greatest range of vision and/or greatest amount of protection from the sun. While embodiments and applications have been shown and described, it would be apparent to those skilled in the art that many more modifications are possible without departing from the inventive concepts herein. The invention, therefore, is not to be restricted except in the spirit of the appended claims.

What is claimed is:

1. A sports visor comprising:
a sweatband having an outside face and an inside face, the inside face being adapted to contact a wearer's forehead, wherein said outside face has affixation means for retaining a removable visor in various locations thereon; and
a thin visor having a top face and a bottom face wherein one distal portion of said bottom face includes a securing means for securing said visor in various positions on said outside face of said sweatband;
whereby said visor avoids contact with the wearer's forehead when affixed to the sweatband.

2. A sports visor according to claim 1 wherein said affixation means is visible when said visor is secured to said affixation means.

3. A sports visor according to claim 1 wherein said affixation means is a fabric-like material covering at least in part said outside face.

4. A sports visor according to claim 3 wherein said fabric-like material is Velcro-compatible.

5. A sports visor according to claim 1 wherein said inside face of said sweatband is absorbent.

6. A sports visor according to claim 1 wherein said sweatband is comprised of an internal stuffing material at least partly contained by said inside face and said outside face, for transporting moisture from said inside face to said outside face.

7. A sports visor according to claim 1 wherein said sweatband is heavier than said visor.

8. A sports visor according to claim 1 wherein said visor has a thickness less than 0.025 millimeters.

9. A sports visor according to claim 1 wherein said visor weighs less than one ounce.

10. A sports visor according to claim 1 wherein said visor is made of an ultraviolet-resistent material.

11. A sports visor according to claim 1 wherein said visor is made of a transparent material.

12. A sports visor according to claim 1 wherein said visor may be secured in various positions between a top edge and a bottom edge of said sweatband.

13. A sports visor according to claim 1 wherein said securing means is at least one thin strip of Velcro TM-like material connected to a concave edge of said bottom face of said visor.

14. A sports visor comprising:
a sweatband having an outside face and an inside face, the inside faces being adapted for contacting a wearer's forehead, said faces at least partly containing an internal stuffing for transporting moisture from said inside face to said outside face wherein said outside face comprises affixation means for retaining a detachable visor in various locations thereon; and
a visor having a top face and a bottom face wherein said visor is less than 0.025 millimeters thick and is lighter in weight than said sweatband, and wherein said bottom face comprises a securing means attached along a concave edge of said bottom face for securing said visor in various positions on said front face of said sweatband.

15. A sports visor kit comprising:
at least one sweatband, each such sweatband having an outside face and an inside face, said inside face being adapted for contacting a wearer's forehead, wherein said outside face has affixation means for retaining a visor in various locations thereon; and
at least one visor, each such visor having a top face and a bottom face, wherein said bottom face has securing means for securing said visor to an outside face of a sweatband.

16. A sports visor comprising:
a sweatband having an outside face and an inside face, and absorbent stuffing at least partly contained by the outside and inside faces, the stuffing capable of transforming perspiration from the inside face to the outside face, the inside face being adapted for contacting a wearer's forehead, and a front portion of the outside face having fabric-like affixation means;

a thin flexible normally flat plastic visor, the visor having a top face and a bottom face, and the bottom face having a concave edge;

securing means attached at least in part along the concave edge of the bottom face of the visor, and adapted to removably affix the visor to the fabric-like affixation means;

whereby the visor, once affixed to the affixation means, avoids contacting the wearer's forehead, and is flexed in a curved shape.

* * * * *